United States Patent
Dholakia et al.

(10) Patent No.: US 7,960,550 B2
(45) Date of Patent: Jun. 14, 2011

(54) PROCESS FOR PREPARING (S)-(+)-CLOPIDOGREL BASE AND ITS SALTS

(75) Inventors: Parind Narendra Dholakia, Ahmedabad (IN); Mayank Ghanshyambhai Dave, Ahmedabad (IN); Pankaj Ramanbhai Patel, Ahmedabad (IN)

(73) Assignee: Cadila Healthcare Limited, Ahmedabad (IN)

( * ) Notice: Subject to any disclaimer, the term of this patent is extended or adjusted under 35 U.S.C. 154(b) by 244 days.

(21) Appl. No.: 12/446,941

(22) PCT Filed: Jan. 8, 2007

(86) PCT No.: PCT/IN2007/000010
§ 371 (c)(1),
(2), (4) Date: Apr. 23, 2009

(87) PCT Pub. No.: WO2008/062421
PCT Pub. Date: May 29, 2008

(65) Prior Publication Data
US 2010/0016595 A1     Jan. 21, 2010

(30) Foreign Application Priority Data

Nov. 24, 2006   (IN) ................ 1937.MUM.2006

(51) Int. Cl.
*C07D 471/04*     (2006.01)
(52) U.S. Cl. ........................................ 546/114
(58) Field of Classification Search ............ 546/114
See application file for complete search history.

(56) References Cited

U.S. PATENT DOCUMENTS
2005/0256152 A1   11/2005   Doser et al.

FOREIGN PATENT DOCUMENTS
EP   1480985 B1   3/2005
EP   1586575 A2   10/2005
EP   1595884 A2   11/2005

*Primary Examiner* — Patricia L Morris
(74) *Attorney, Agent, or Firm* — IpHorgan Ltd.

(57) ABSTRACT

Processes for the preparation of Methyl (+)-(S)-(2-chlorophenyl)-(6,7dihydro-4H-thieno[3,2-c]pyridin-5-yl)acetate [Clopidogrel base, (I)] and their various pharmaceutically acceptable salts.

18 Claims, No Drawings

PROCESS FOR PREPARING (S)-(+)-CLOPIDOGREL BASE AND ITS SALTS

CROSS-REFERENCE TO RELATED APPLICATIONS

This is a Sect. 371 National Stage of PCT International Application No. PCT/IN2007/000010, filed on 8 Jan. 2007, claiming priority of Indian Patent Application No. 1937/MUM/2006 filed on 24 Nov. 2002, the contents of both applications hereby being incorporated by reference.

FIELD OF INVENTION

The present invention relates to an improved process for the preparation of Methyl (+)-(S)-(2-chlorophenyl)-(6,7dihydro-4H-thieno[3,2-c]pyridin-5-yl)acetate [Clopidogrel base, (I)] and their various pharmaceutically acceptable salts.

BACKGROUND TO THE INVENTION

Clopidogrel (S-(+)-(2-chlorophenyl)-(6,7-dihydro-4H-thieno[3,2-c]pyridin-5-yl) acetic acid methyl ester has the following structure (1)

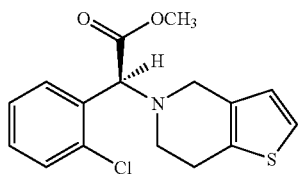

(I)

It is available in the market as its bisulfate salt and is marketed by Sanofi-Synthelabo as "Plavix".

Clopidogrel is an inhibitor of platelet aggregation and is marketed as an antianginal agent, antiplatelet agent and is found to decrease morbid events in people with established atherosclerotic cardiovascular disease and cerebrovascular diseases.

The therapeutic application of Clopidogrel as blood-platelet aggregation inhibiting agents and antithrombotic agent and its preparation is disclosed in U.S. Pat. Nos. 4,529,596. 4,847,265 describes the process for the preparation of the hydrogen sulfate salt of Clopidogrel wherein first the racemic base is obtained which is then resolved using (–) Camphor sulfonic acid [(–) CSA] to obtain the chirally pure base which is then converted to the corresponding salts such as sulfate, hydrochloride etc. salts.

Various other strategies to prepare Clopidogrel are disclosed in WO 98/51681, WO 98/51682, WO 98/51689, WO 99/18110, U.S. Pat. Nos. 5,036,156, 5,132,435, 5,139,170, 5,204,469 and 6,080,875 etc. all of which are incorporated herein as reference.

We have earlier disclosed improved processes for the manufacture of (S)-(+)-Clopidogrel base, its intermediates and its bisulfate salt [Indian Patent Applications 84/MUM/2001 (WO 02059128/U.S. Pat. No. 6,635,763), & 335/MUM/2001] which are cited herein in their entirety as reference. The process described therein may be represented as:

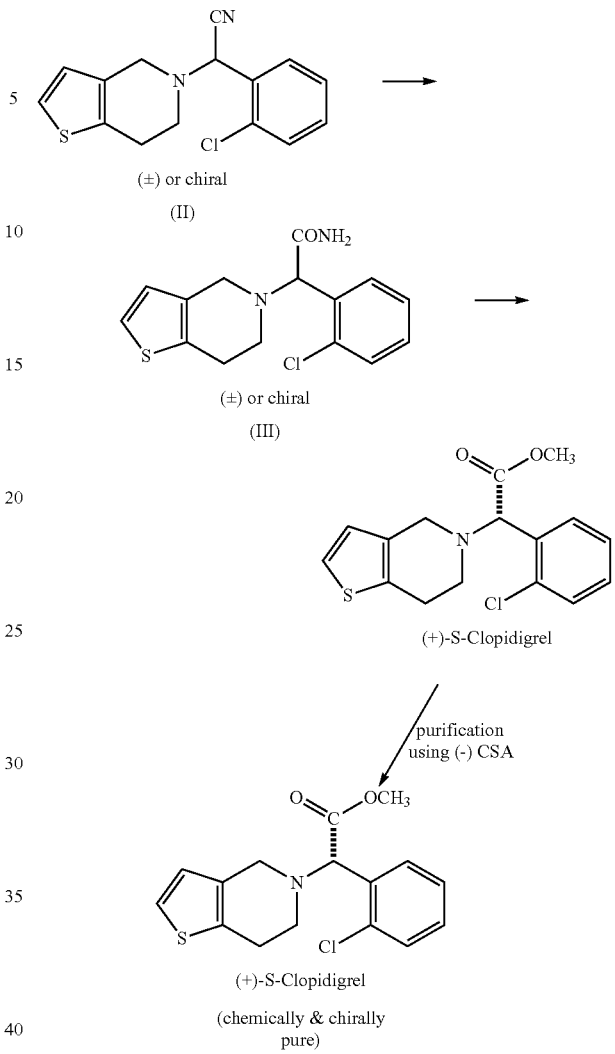

EP 1480985 (Helm AG) describes a process for purifying impure Clopidogrel base by treating the impure base with benzenesulfonic acid and subsequently hydrolyzing the salt to obtain the pure base.

In all prior art process, the Clopidogrel base needs to be resolved/chirally enriched using (–)-Camphor sulfonic acid salt. Such a process is expensive and hence industrially less suitable. The present inventors have surprisingly found that chemically and chirally pure Clopidogrel base can be prepared without the need for further treatment with camphor sulfonic acid, which is costly and less viable. The base so prepared could be used for preparing different salts.

We herein describe a novel process for preparing optically pure Clopidogrel base which does not require subsequent purification step, and is easy to scale up and operationally simple.

SUMMARY OF THE INVENTION

The present invention provides an improved process to prepare Clopidogrel base and its corresponding salts, of general formula (I). The present invention especially provides a process to prepare chemically and optically pure Clopidogrel base and its pharmaceutically acceptable salts.

All prior art process requires that the Clopidogrel base (I) is either resolved or chirally enriched using (−) Camphor sulfonic acid [(−) CSA]. The process involved treatment of the base with (−) CSA, to obtain the corresponding salt, resolving &/or chirally enrichment and subsequent basification to obtain the (+)-(S) isomer. However, this process is costly due to the high cost of camphor sulfonic acid. We herein describe a method which does not require the use of (−) CSA. The method may be described as below:

The salts are separated based on their differential solubility in the solvent. The salt of the (S)-isomer is subsequently broken using suitable inorganic bases to obtain (S)-Clopidogrel base (I) with high chemical and chiral purity. Suitable inorganic bases may be selected from ammonia, sodium hydroxide, potassium hydroxide, sodium or potassium carbonates, sodium bicarbonate and the like. The temperature of the reaction is suitably controlled.

Scheme:

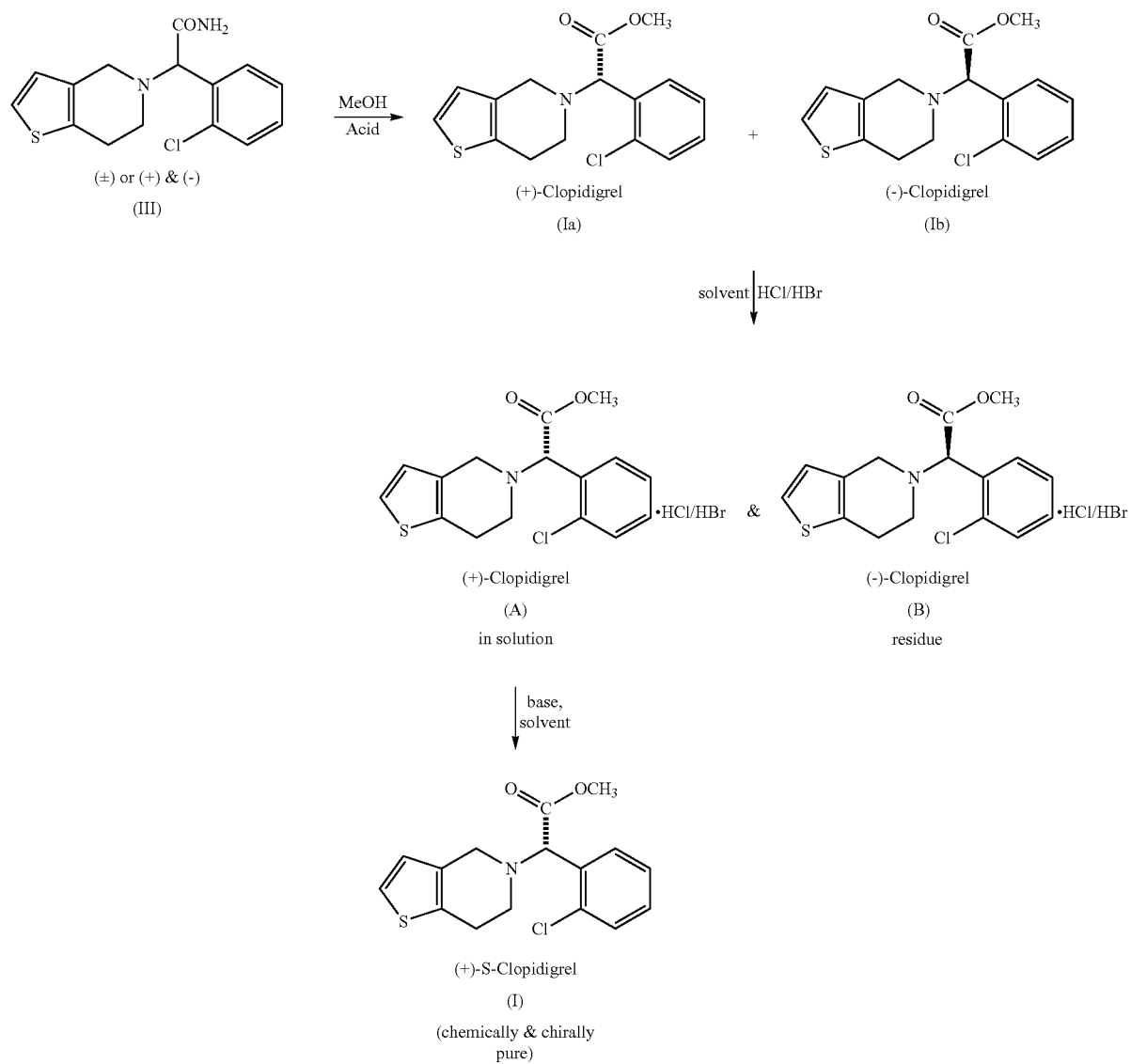

a) an amide of formula (III) in either (±) form or varying mixtures of its optically active (+) and (−) forms, is treated with methanol and suitable acids in suitable solvents to obtain Clopidogrel base (Ia & Ib). Suitable acids may be inorganic acids such as sulfuric acid or organic acids such as methane sulfonic acid or benzene sulfonic acid.

b) The base is treated with suitable inorganic acids such as hydrochloride acid or hydrobromic acid in suitable solvents to obtain the corresponding salts [(A) & (B) resp.].

The amide of formula (III) may be prepared according to processes known in the art, preferably it is prepared according to the process described in U.S. Pat. No. 6,635,763 and in our application 914/Mum/2006.

In a preferred embodiment the starting amide is chirally enriched worst the (S)-(+)-isomer. In a further preferred embodiment, the starting material is chirally pure (S)-(+)-amide.

The pure base may further be converted to corresponding salts such as bisulfate, hydrochloride, hydrobromide, mesylate, besylate, tosylate and the like by reacting the base with the corresponding acids in suitable solvents by techniques known.

The present invention is further exemplified by the following examples which are representative of the preferred mode as envisaged by the inventors and should not be construed as restricting the scope of the invention in any way.

EXAMPLE 1

5.6 g of (+)α-(4,5,6,7-tetrahydrothieno[3,2-c]-5-pyridyl)-α-2-chlorophenyl]acetamide (III) was refluxed in methanol for ~60 h in presence of sulfuric acid. The reaction mixture was cooled, aqueous solution of sodium bicarbonate added to the suspension and alkaline aqueous phase extracted with dichloromethane. The organic layer separated, washed with water and evaporated to obtain Clopidogrel base (Ia & Ib). The base was dissolved in ethyl acetate and treated with dry HCl (g) to get Clopidogrel hydrochloride 5 g [R isomer 8%], it was dissolved in acetone (=50 mL), stirred and heated at 60-65° C. to get a clear solution The reaction mixture was cooled to 20-25° C., stirred for 16 to 18 hrs. and filtered (R isomer as solid residue, 45%) & washed with acetone. Mother liquor was distilled off to get a sticky solid 4.8 g (R isomer 1%). The reaction mixture was dumped into a mixture of dichloromethane-water, and to this was added 10% $NaHCO_3$ solution mixture at low temperature with stirring at pH ~8-9. Organic layer was separated and aqueous layer extracted with dichloromethane. The combined organic layer was washed with water, stirred with activated charcoal and sodium sulphate and hyflow filtered, washed with dichloromethane and distilled off at 50-52° C. and traces removed using reduced pressure to obtain (S)-(+) Clopidogrel base as a pale yellow oil.
wt=4.28 g (R isomer 1%, chiral purity 99%)

EXAMPLE 2

Clopidogrel base 5g [(I), R isomer 4%] was dissolved in acetone (50 ml), cooled and HCl gas passed till pH 1. The reaction mixture was stirred at 20-25° C. for ~16-18 hrs. The mixture was partly distilled and stirred for another 3 hours, filtered (R isomer as solid residue, 31%), & washed with acetone. Mother liquor was distilled off to get sticky solid 4.9 g (R isomer 2.5%). The reaction mixture was dumped into dichloromethane-water and to this was added 10% $NaHCO_3$ solution (50 ml) at low temperature with stirring, pH was maintained at ~8-9. Organic layer separated and aqueous layer extracted with dichloromethane. The combined organic layer was washed with water, stirred with activated charcoal (1.0 g) and sodium sulphate and hyflow filtered, washed with dichloromethane and distilled off at 50-52° C. and traces removed under reduced pressure to get oil. The (S)-(+) Clopidogrel base was obtained as a pale yellow oil. (wt=4.3 g, R isomer 2.5%, chiral purity 97.5%)

EXAMPLE 3

25 g of (+)α-(4,5,6,7-tetrahydrothieno[3,2-c]-5-pyridyl)-α-2-chlorophenyl]acetamide (III) was refluxed in methanol for ~60 h in presence of sulfuric acid. The reaction mixture was cooled, aqueous solution of sodium bicarbonate was added to the suspension and alkaline aqueous phase extracted with dichloromethane. The organic layer was separated, washed with water and evaporated to Clopidogrel base. The base was dissolved in ethyl acetate and treaded with dry HCl (g) to get Clopidogrel hydrochloride 24 g (R isomer 2.5%) The salt was stirred in ethyl acetate (48 ml) and acetone (480 ml) at 20-25° C., filtered [R isomer as solid residue, 45%] & washed with acetone. Mother liquor was distilled off to get sticky solid 22 g (R isomer 1.6%) The reaction mixture was dumped into DCM-water and 10% $NaHCO_3$ solution was added to the mixture at low temperature with stirring at pH ~8-9. Organic layer separated and aqueous layer extracted with dichloromethane. The combined organic layer Was washed with water, stirred with activated charcoal (5 g) and sodium sulphate and hyflow filtered, washed with dichloromethane and distilled off at 50-52° C. and traces removed using reduced pressure to obtain the pure base as a pale yellow oil (wt=19.7 g, R isomer 1.6%, chiral purity 98.4%).

EXAMPLE 4

5 g (+)α-(4,5,6,7-tetrahydrothieno[3,2-c]-5-pyridyl)-α-2-chlorophenyl]acetamide (III) was taken in 25 ml methanol, stirred and to this 25 g benzene sulfonic acid was added to the mixture. The resulting solution was refluxed for 10-24 hours. The solvent was removed and the residue was basified using aqueous sodium bicarbonate solution in dichloromethane. The compound of formula (I) was obtained with chiral enrichment after removal of dichloromethane.

The Clopidogrel base obtained is treated as per the process described in Example 2 to obtain (S)-(+) Clopidogrel base in chemically and chirally pure form.

EXAMPLE 5

100 g (+)α-(4,5,6,7-tetrahydrothieno[3,2-c]-5-pyridyl)-α-2-chlorophenyl]acetamide (III) was taken in 500 ml methanol, stirred and subsequently 470 g methanesulfonic acid was added to the mixture. The resulting solution was refluxed for 20-40 hours. The solvent was removed and the residue was basified using aqueous sodium bicarbonate solution in dichloromethane. The compound of formula (I) was obtained with chiral enrichment after removal of dichloromethane The Clopidogrel base (I) obtained is treated as per the process described in Example 2 to obtain (S)-(+) Clopidogrel base in chemically and chirally pure form.

The (+)-(S) Clopidogrel base may be used to prepare the corresponding salts selected from bisulfate, hydrochloride, hydrobromide, mesylate, besylate, tosylate and the like by reacting the base with the corresponding acids in suitable solvents by techniques known.

Advantages of the Present Process

The process of the present invention has following advantages:
1) The process does not require the use of camphor sulfonic acid, which is very expensive.
2) The reagents and chemicals used are readily available.
3) The reactions conditions employed during the various steps are mild.
4) Easy to scale up
5) No requirement of subsequent resolution or further purification

We claim:
1. A process for purification of Clopidogrel base comprising the steps of
   i) treating Clopidogrel base (I) in either (±) form or a mixture of its (+) & (−) isomer in suitable solvent(s) with suitable inorganic acid(s) selected from HCl or HBr to obtain the corresponding salts (A) & (B) respectively;
   ii) separating the salts of the stereoisomers based on their differential solubility in suitable solvents;

iii) neutralizing the salt of the (S)-isomer by treatment with suitable inorganic base to obtain the (S)-(+) Clopidogrel base.

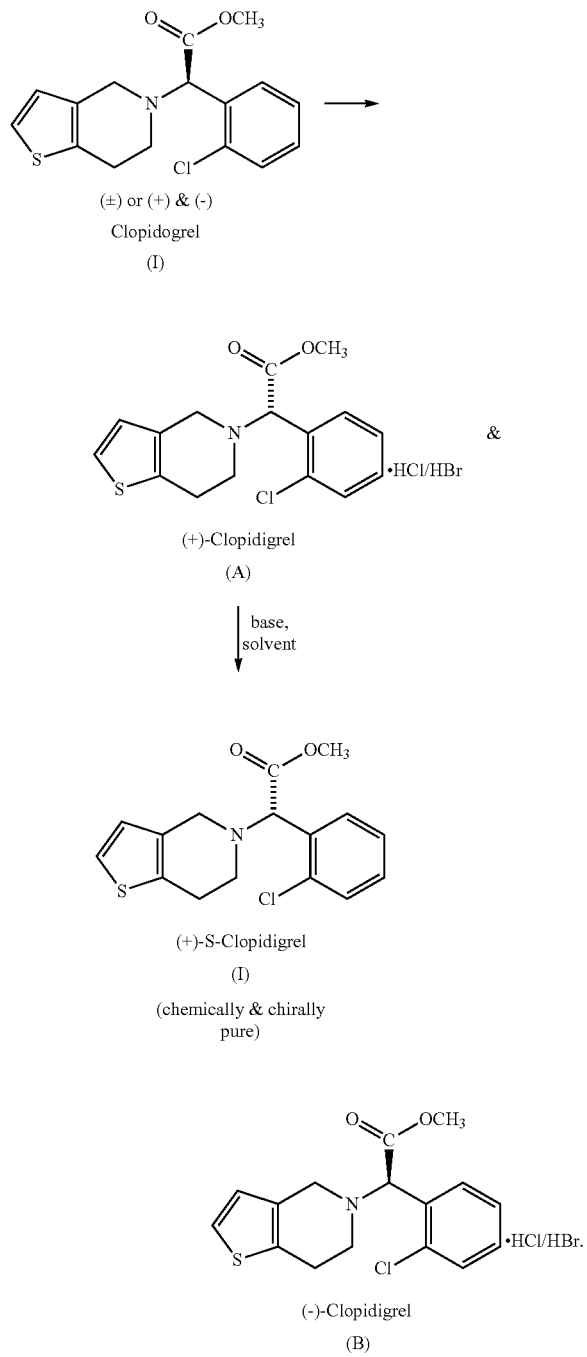

2. A process as claimed in claim 1 wherein the mixture of Clopidogrel base is chirally enriched with respect to the (S)-(+) isomer.

3. A process as claimed in claim 1 wherein the suitable solvent may be selected from a group consisting of ethyl acetate, acetone, dichloromethane or their mixtures thereof.

4. A process as claimed in claim 1 wherein a mixture containing varying ratios of the two enantiomers, (−)-I and (+)-I is chirally enriched to (+)-(I)-stereoisomer, or chiral removal of (−)-(I) enantiomer from a variable mixture of (−)-I and (+)-I stereoisomers.

5. A process as claimed in claim 1 wherein the Clopidogrel base is prepared by treating a compound of formula (III) in either (±) form or its optically active (+) or (−) forms, with acidic reagents in the presence of methanol to obtain a compound of formula (I)

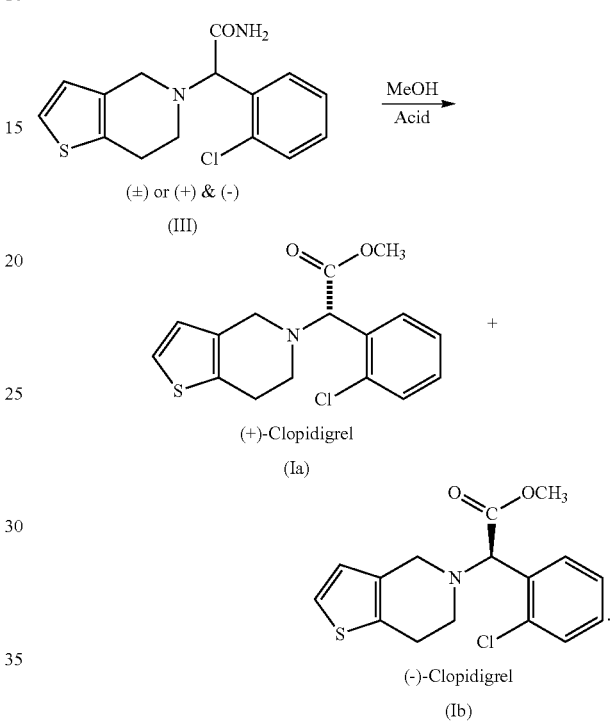

6. A process as claimed in claim 5 wherein the acidic reagents are selected from the group consisting of sulfuric acid, methane sulfonic acid or benzene sulfonic acid or any mixtures thereof.

7. A process as claimed in claim 1 wherein the (+)-(S) Clopidogrel base is further converted to its suitable pharmaceutically acceptable salts by treating the base with a corresponding acid.

8. The process according to claim 2 wherein the suitable solvent may be selected from a group consisting of ethyl acetate, acetone, dichloromethane or their mixtures thereof.

9. The process as claimed in claim 2 wherein a mixture containing varying ratios of the two enantiomers, (−)-I and (+)-I is chirally enriched to (+)-(I)-stereoisomer, or chiral removal of (−)-(I) enantiomer from a variable mixture of (−)-I and (+)-I stereoisomers.

10. The process as claimed in claim 3 wherein a mixture containing varying ratios of the two enantiomers, (−)-I and (+)-I is chirally enriched to (+)-(I)-stereoisomer, or chiral removal of (−)-(I) enantiomer from a variable mixture of (−)-I and (+)-I stereoisomers.

11. The process as claimed in claim 3 wherein the Clopidogrel base is prepared by treating a compound of formula (III) in either (±) form or its optically active (+) or (−) forms, with acidic reagents in the presence of methanol to obtain a compound of formula (I)

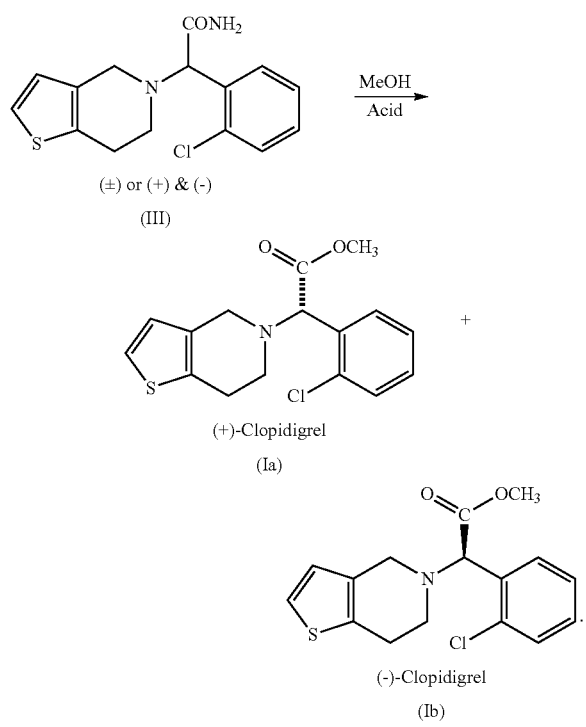

12. The process as claimed in claim 4 wherein the Clopidogrel base is prepared by treating a compound of formula (III) in either (±) form or its optically active (+) or (−) forms, with acidic reagents in the presence of methanol to obtain a compound of formula (I)

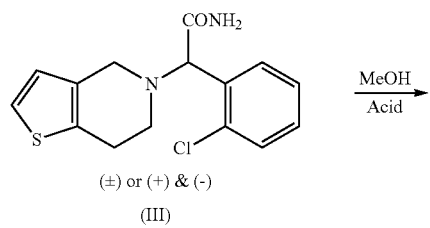

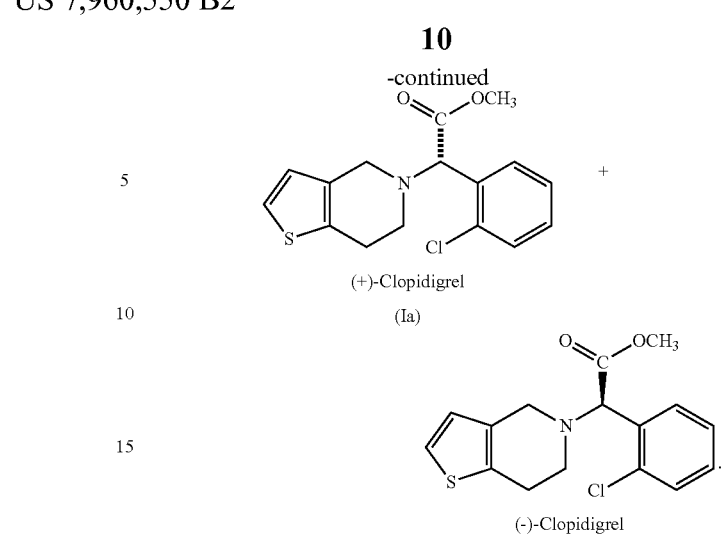

13. The process as claimed in claim 11 wherein the acidic reagents are selected from the group consisting of sulfuric acid, methane sulfonic acid or benzene sulfonic acid or any mixtures thereof.

14. The process as claimed in claim 2 wherein the (+)-(S) Clopidogrel base is further converted to its suitable pharmaceutically acceptable salts by treating the base with a corresponding acid.

15. The process as claimed in claim 3 wherein the (+)-(S) Clopidogrel base is further converted to its suitable pharmaceutically acceptable salts by treating the base with a corresponding acid.

16. The process as claimed in claim 4 wherein the (+)-(S) Clopidogrel base is further converted to its suitable pharmaceutically acceptable salts by treating the base with a corresponding acid.

17. The process as claimed in claim 5 wherein the (+)-(S) Clopidogrel base is further converted to its suitable pharmaceutically acceptable salts by treating the base with a corresponding acid.

18. The process as claimed in claim 6 wherein the (+)-(S) Clopidogrel base is further converted to its suitable pharmaceutically acceptable salts by treating the base with a corresponding acid.

* * * * *